(12) United States Patent
Reuscher et al.

(10) Patent No.: US 8,481,716 B2
(45) Date of Patent: Jul. 9, 2013

(54) PROCESS FOR PREPARING AN ALPHA-LIPOIC ACID/CYCLODEXTRIN COMPLEX AND PRODUCT PREPARED

(75) Inventors: Helmut Reuscher, Onsted, MI (US); Mark Bauer, Adrian, MI (US)

(73) Assignee: Wacker Chemie AG, Munich (DE)

( * ) Notice: Subject to any disclaimer, the term of this patent is extended or adjusted under 35 U.S.C. 154(b) by 222 days.

(21) Appl. No.: 12/768,976

(22) Filed: Apr. 28, 2010

(65) Prior Publication Data

US 2010/0210716 A1 Aug. 19, 2010

Related U.S. Application Data

(62) Division of application No. 11/302,810, filed on Dec. 14, 2005, now Pat. No. 7,737,269.

(30) Foreign Application Priority Data

Dec. 17, 2004 (EP) .................................. 04400070

(51) Int. Cl.
*C08B 37/16* (2006.01)
*A01N 51/00* (2006.01)
*A61K 31/655* (2006.01)

(52) U.S. Cl.
USPC ............................................ 536/103; 214/58

(58) Field of Classification Search
None
See application file for complete search history.

(56) References Cited

U.S. PATENT DOCUMENTS

| 5,288,916 A | 2/1994 | Lorenz et al. |
| 5,702,724 A | 12/1997 | Stahl et al. |
| 2004/0266858 A1 | 12/2004 | Schuhbauer et al. |

FOREIGN PATENT DOCUMENTS

| CA | 2135535 | 5/1995 |
| EP | 0 654 484 A2 | 5/1995 |
| EP | 1 514 877 A1 | 3/2005 |
| JP | 07188304 | 7/1995 |
| WO | 00/64440 A1 | 11/2000 |
| WO | 02098423 | 12/2002 |
| WO | 03047567 | 6/2003 |

OTHER PUBLICATIONS

Szejtli, Medicinal Research Reviews, vol. 14, No. 3, 353-386 (1994)).*
Trentin et al, "Capillary zone electrophoresis study of cyclodextrin—lipoic acid host-guest interaction", Electrophoresis 2002, 23, pp. 4117-4122.
Tong Lin-Hui, Pang Zheng-Zhi and Yi Ying, "Inclusion Complexes of α- and β-Cyclodextrin with α-Lipoic Acid", Journal of Inclusion Phenomena and Molecular Recognition in Chemistry, vol. 23, 1995, pp. 119-126.
Derwent Abstract Corresponding to EP 0 654 484 A2, 1995.
Heng L. Jin et al., Optical Enrichment of Dansyl-rac-Amino Acids by formation of Crystalline Inclusion Complexes with Cyclodextrins, Chirality 1:137-141 (1989); 5 pages.
Centre College CHE 24 Lab Manual, Fall 1998, from http://web.centre.edu/che/nmr_workshop/24_lab_manual.htm.

* cited by examiner

*Primary Examiner* — Layla Bland
(74) *Attorney, Agent, or Firm* — Brooks Kushman P.C.

(57) ABSTRACT

The invention relates to a process for the preparation of a cyclodextrin/alpha-lipoic acid complex, wherein in a first step, an alpha-lipoic acid and a cyclodextrin are dissolved in an aqueous alkaline solution having a pH above pH 7, and in a second step an acid is added to lower the pH of the solution to a pH below pH 7.

20 Claims, No Drawings

PROCESS FOR PREPARING AN ALPHA-LIPOIC ACID/CYCLODEXTRIN COMPLEX AND PRODUCT PREPARED

CROSS-REFERENCE TO RELATED APPLICATIONS

This application is division of U.S. application Ser. No. 11/302,810 filed Dec. 14, 2005 now U.S. Pat. No. 7,737,269, issued Jun. 15, 2010. The disclosure of which is incorporated in its entirety by reference herein.

BACKGROUND OF THE INVENTION

1. Field of the Invention

The invention relates to a process for preparing an alpha-lipoic acid/cyclodextrin complex and product prepared.

2. Background Art

Cyclodextrins are cyclic oligosaccharides composed of 6, 7 or 8 α(1-4)-linked anhydroglucose units. The α-, β- or γ-cyclodextrins, which are prepared for example by enzymatic conversion of starch, differ in the diameter of their hydrophobic cavity and are generally suitable for inclusion of numerous lipophilic substances.

Alpha-lipoic acid (Thioctic Acid) is a naturally occurring molecule produced by both plants and animals. It serves as a cofactor for some enzymes and as an excellent antioxidant/free radical scavenger. Since it has been known that alpha-Lipoic Acid can improve insulin sensitivity in cases of Type II diabetes, alpha-Lipoic Acid has been employed for treating diabetes as well as alcoholic liver disease and other neuropathies.

Alpha-lipoic acid is a lipid-soluble substance. It is a yellowish powder and is unstable in light. Its solubility in water is very poor. A formulation with cyclodextrins, especially with alpha cyclodextrin, is stable to temperature and light and increases the dispersibility in water and the bioavailability. The complexes also reduce the unpleasant odour of alpha-lipoic acid.

The complexation of lipoic acid with α-cyclodextrin and β-cyclodextrin using a solution method is described in the Journal of Inclusion Phenomena and Molecular Recognition in Chemistry, (1995), vol. 23, pp. 119-96. The processes described therein for preparing a cyclodextrin complex with alpha-lipoic acid show various disadvantages in the laboratory and production scale. On use of the solution method on the production scale, the amount of water needed to solubilize the cyclodextrin is enormous. For economic reasons, therefore, these methods cannot be used commercially to prepare a cyclodextrin/alpha-lipoic acid complex. According to this literature the thermal stability of alpha-lipoic acid can be improved significantly by its inclusion in beta cyclodextrin. Calculation of the stability constants for the alpha-lipoic acid/cyclodextrin complex according to the Benesi-Hildebrand procedure are described also on page 121 of this paper. The calculated stability constants for the cyclodextrin complex with alpha cyclodextrin were 3.34 and for the beta cyclodextrin complex 3.95. According to these findings the beta cyclodextrin complex is more stable than the alpha cyclodextrin alpha-lipoic acid complex.

In Canadian patent application 2,135,535 a process is described characterized in that thioctic acid is suspended in water, cyclodextrins are added at elevated temperature such as 50° C., stirred for several hours, cooled down and the inclusion compound is isolated by filtration and vacuum dried. Working in suspension to produce cyclodextrins complexes requires elevated temperatures and long complexation times for efficient results. Elevated temperatures can have a negative impact on the stability of the alpha-lipoic acid.

SUMMARY OF THE INVENTION

It is an object of the present invention to provide a process which allows preparation of a cyclodextrin/alpha-lipoic acid complex in a rapid and uncomplicated manner, even at room temperature, without the disadvantages of the prior art. These and other objects are achieved by a two step process which comprises dissolving an alpha-lipoic acid and a cyclodextrin in an aqueous alkaline solution having a pH above 7, followed by step adding an acid to lower the pH of the solution to a pH below pH 7. By this process a mixture of solids in water comprising the cyclodextrin/alpha-lipoic acid complex is obtained without high temperatures and long mixing times. The costs of the production process are reduced significantly.

DETAILED DESCRIPTION OF THE PREFERRED EMBODIMENT(S)

The cyclodextrins used are α-, β-, or γ-cyclodextrin, preferably β- or α-cyclodextrin, most preferably α-cyclodextrin. The alpha-lipoic acid used is either racemic or enantiomerically pure. The solvent is preferably a water/alcohol mixture, most preferably water.

The process preferably starts from an aqueous alpha-lipoic acid solution above pH 7 to which the cyclodextrin is added. However, it is equally possible to prepare an aqueous cyclodextrin solution above pH 7 first and to add lipoic acid thereto. The pH of the aqueous solution during the first step is preferably between pH 10 and pH 14, more preferably between pH 13 and pH 14, or at pH 14. The pH above pH 7 is preferably adjusted by using a suitable base, most preferably a base selected from among ammonium hydroxide, sodium hydroxide, and potassium hydroxide. The solubilization of the alpha-lipoic acid and the cyclodextrin in the first step is effected using a base and standard mixing equipment. It should be noted that when amorphous silica is employed as a flowing agent in either reactant, the solution will still be slightly cloudy.

The solids content of the aqueous solution in the first step is preferably less than 50% (w/w). The solids content can be calculated by dividing the sum of the dry weights of the cyclodextrin, alpha-lipoic acid, and base, by the overall weight of the mixture. The aqueous mixture in this first step preferably contains a solids content between 10 and 50% by weight, more preferably between 20 and 40%, and most preferably between 25 and 35%.

The molar ratio cyclodextrin to alpha-lipoic acid is preferably between 2.0 and 1.0, more preferably between 1.5 to 1.0, yet more preferably between 1.2 and 1.0, and most preferably between 1.15 and 1.0.

The process of the invention preferably takes place in a temperature range of 10-40° C., more preferably at 15-30° C., and most preferably at about 25° C. The complexation ordinarily takes place under atmospheric pressure. The reaction (complexation) time of the first step of the process is preferably below 3 h, more preferably below 2 h, and most preferably below 1 h.

In the second step of the process according to the present invention the formed alpha-lipoic acid/cyclodextrin complex is precipitated by addition of an acid. An inorganic or organic acid may be used, preferably an inorganic or organic acid selected from among hydrochloric acid, sulphuric acid, phosphoric acid, acetic acid, citric acid, and ascorbic acid. Especially preferred are hydrochloric acid, sulphuric acid, and phosphoric acid.

The second turns the lipoic acid back to its acid form, precipitates the complex and brings the pH of the final aqueous mixture below pH 7. The final pH of the aqueous mixture in this second step is thus preferably between pH 6 and pH 3, more preferably between pH 5 and pH 3.

The complex can be used directly in the form of the reaction mixture, however, it may also be isolated e.g. by filtration, centrifugation, belt drying, or spray-drying methods, and processed to give a stable powder. The complex is preferably dried by oven drying, spray drying, filtration or belt drying, most preferably by spray-drying in a spray dryer having an inlet temperature higher than 160° C. and an outlet temperature below 100° C., yielding a fine yellow-white powder. The inlet spray drying temperature preferably is higher than 170° C. with an outlet temperature below 90° C., most preferably higher than 180° C. with an outlet temperature below 80° C.

The alpha-lipoic acid/cyclodextrin complexes produced according to this invention show a higher degree of complexation and provide better temperature stability in powder form than complexes produced by the methods. Therefore the invention also relates to an alpha-lipoic acid/cyclodextrin complex produced according to the process of the present invention. An alpha-lipoic acid complex produced according to the present invention contains less than 10% of non-complexed material, preferably less than 8%, and most preferably less than 5% measured using Differential Scanning Calorimetry (see e.g. example 7).

By contrast, an alpha-lipoic acid/cyclodextrin complex produced according to the Canadian patent application 2,135,535 shows about 28% of non-complexed alpha-lipoic acid (see comparison example and example 7). The method of the present invention produces an alpha-lipoic acid/cyclodextrin complex with significantly lower percent of non-complexed alpha-lipoic acid, even up to 100% complexation rate (see example 7). The superiority of complexes produced according to the method described in this patents leads to significantly higher temperature stability (see example 8, 9, and 10).

According to published heating experiments, at 100° C. the half life of lipoic acid at 100° C. is 5.2 h. For the alpha-lipoic acid/beta cyclodextrin complex it is 73 h (see Journal of Inclusion Phenomena and Molecular Recognition in Chemistry, (1995), vol. 23, page 122 and FIG. 4). From these measurements it can be calculated the beta CD complex is about 14 times more stable at 100° C. (73h/5.2h) than the alpha-lipoic acid itself. The alpha cyclodextrin/alpha-lipoic acid complex according to the present invention shows a half life of more than 213 days and is thus at least 70 times more stable than the lipoic acid itself (see example 10).

The complex according to the present invention may be used in pharmaceutical formulations, dietary supplements, and nutraceutical, or functional food formulations.

The following examples are intended to illustrate the invention in greater detail, but should not be construed as limiting the scope of the invention in any way. The α-, β-, and γ-cyclodextrins can be purchased under the name Cavamax™ cyclodextrins from Wacker-Chemie, Munich, Germany. Alpha-lipoic acid can be purchased from Degussa, Freising, Germany. The lipoic acid may also contain a flowing agent such as amorphous silica.

COMPARISON EXAMPLE C1:

(According to example 7 of the Canadian Patent Application 2,135,535)

172.8 g alpha cyclodextrin containing approx. 10% water were dissolved in 700 g water at 50° C. 3.3 g Sodium ascorbate was added and dissolved in the alpha cyclodextrin solution. 33.01 g sieved thioctic acid was added to the alpha cyclodextrin solution and stirred 3 hours at 50° C. The suspension was then filtered and the filtrate was cooled (50° C. 12 h). The precipitate hereby formed was separated by filtration and dried in a vacuum oven at 30°. This product contained 15.8% alpha-lipoic acid by weight according to HPLC analysis (see example 6) and was used for comparison purposes in examples 7 and 10.

EXAMPLE 1

Preparation of a Cyclodextrin Alpha-Lipoic Acid Alpha Cyclodextrin Complex 117.2 g of a 45% potassium hydroxide solution (0.940 mol) was added to 5.0 kg water and mixed at room temperature until clear. 194.0 g alpha-lipoic acid (99%, 0.931 moles) was added to the potassium hydroxide solution and mixed until clear. 1,046.0 g alpha cyclodextrin (9.25% water content, 0.977 moles) was added and stirred 3 hours until slightly cloudy to clear (in case of the amorphous silica as flowing agent the solution will be slightly cloudy). 0.940 mol of 12 N hydrochloric acid was slowly added until the pH reached pH 3 to precipitate the complex. The final aqueous mixture is spray dried immediately at 180° C.

EXAMPLE 2

Preparation of an Alpha-Lipoic Acid/Alpha Cyclodextrin Complex 186.7 g of a 45% potassium hydroxide solution (1.498 moles) was added to 3910 g water and mixed at room temperature until clear. 300 g alpha-lipoic acid (99%, 1.439 moles) was added to the potassium hydroxide solution and mixed until clear clear (in case of the presence of amorphous silica as flowing agent the solution will be slightly cloudy). 1,572 g alpha cyclodextrin (at 9.25% water 1.468 moles) was added and stirred for 3 hours at room temperature until no further clarification was seen. 1.498 moles of 37% hydrochloric acid was added to precipitate the complex. With a minimal molar excess of hydrochloric acid in comparison to the potassium hydroxide used, the final pH of the solution was at pH 3. The final aqueous mixture was spray dried immediately at 180° C.

EXAMPLE 3

Preparation of an Alpha-Lipoic Acid/Alpha Cyclodextrin Complex 1.44 moles of potassium hydroxide were added to 5.5 kg of water and mixed at room temperature until clear. The pH of this solution was at pH 14. 300 g alpha-lipoic acid (98%, 1.425 moles) was added to the potassium hydroxide solution and mixed until clear (in case of the presence of amorphous silica as flowing agent the solution will be slightly cloudy). 1.553 kg of dry alpha cyclodextrin (1.598 moles) was added and stirred 50 minutes at room temperature. 1.44 moles of 37% hydrochloric acid was added precipitating the complex. This mixture was stirred 30 minutes at room temperature. The final pH was at about pH 3. This aqueous mixture was spray dried immediately at about 180° C. inlet and about 80° C. outlet temperature.

EXAMPLE 4

Preparation of an Alpha-Lipoic Acid/Alpha Cyclodextrin Complex 23.9 g of a 45% potassium hydroxide solution (0.192 moles) was added to 767 g water and mixed at room temperature until clear. 40.0 g alpha-lipoic acid (98%, 0.190 moles) was added to the potassium hydroxide solution and mixed at room temperature until clear (in case of the presence of amorphous silica as flowing agent the solution will be slightly cloudy). 221.7 g alpha cyclodextrin (9.2% water content, 0.207 moles) was added and stirred for 60 minutes at room temperature. 0.192 moles of 37% hydrochloric acid was added to precipitate the complex. With a minimal molar excess of hydrochloric acid in comparison to the potassium hydroxide used the final pH of the solution was about pH 3. The final aqueous mixture is spray dried immediately at 180° C.

EXAMPLE 5

Preparation of an Alpha-Lipoic Acid/Alpha Cyclodextrin Complex 29.95 kg of potassium hydroxide pellets (87.9%, 469.3 moles) were added to 1920.0 kg of water and mixed at room temperature until clear. The pH of this solution was at pH 14. 97.8 kg alpha-lipoic acid (98%, 464.5 moles) was added to the potassium hydroxide solution and mixed until clear (in case of the presence of amorphous silica as flowing agent the solution will be slightly cloudy). 555.1 kg alpha cyclodextrin (8.9% water content, 520.3 moles) was added and stirred 60 minutes at room temperature. 469.3 moles of 37.7% hydrochloric acid was added precipitating the complex. This mixture was stirred 55 minutes at room temperature. The final pH was at about pH 3. The final aqueous mixture was spray dried immediately at about 180° C. inlet and about 80° C. outlet temperature.

EXAMPLE 6

High-Performance Liquid Chromatography Analysis

The alpha-lipoic acid/cyclodextrin complexes were analyzed for content using High-Performance Liquid Chromatography (HPLC). The column used is a 25 mm C 18, and the conditions are as follows: UV detector at wavelength 215 nm, flowrate 0.8 ml/min. Mobile phase is 585 ml ethanol, 90 ml Acetonitrile, 455 ml 0.05 mol potassium dihydrogen phosphate ($KH_2PO_4$), adjusted to pH 3.0-3.1 with phosphoric acid ($H_3PO_4$). The injection volume was 20 microliters (µl) and the column temperature 30° C. Under these conditions the retention time for alpha-lipoic acid is approximately 6.5 minutes.

Procedure:

150 mg of cyclodextrin complex was sonicated for 60 seconds in 50 ml acetonitrile. 40 ml water was added and sonicated for another 30 seconds. The solution was transferred to a 100 ml volumetric flask and filled to the mark with water. This solution was then tested by HPLC and the alpha-lipoic acid content content calculated using a multipoint calibration curve prepared from a known standard.

Results:

| HPLC Samples | Alpha-lipoic Acid Content (w/w) [%] |
| --- | --- |
| Comparison Example C1 | 15.8 |
| Example 1 | 13.4 |
| Example 2 | 13.6 |
| Example 3 | 12.5 |
| Example 4 | 13.5 |
| Example 5 | 12.7 |

EXAMPLE 7

Differential Scanning Calorimetry Analysis for Uncomplexed Alpha-Lipoic Acid

Cyclodextrin complexes (3-6 mg sample size) were analyzed using Differential Scanning Calorimeter (DSC). Samples were scanned for an alpha-lipoic acid (ALA) melting peak around 60° C. This peak, if present, was compared to a peak at this temperature of pure alpha-lipoic acid to calculate percentage of uncomplexed alpha-lipoic acid in the complex. Taking the sample size and the alpha-lipoic acid content of the sample into account from the area under the curve ("AUC") the melting energy in J/g for uncomplexed alpha-lipoic acid can be calculated. The peak around 60° C. decreases with increasing degree of complexation. A cyclodextrin complex containing no uncomplexed alpha-lipoic acid shows no melting peak around 60° C.

Results:

| | Content ALA [%] | Sample Weight [mg] | AUC at 60° C. [mJ] | Peak at 60° C. [J/g] | Non Complexed ALA [%] | Complexed ALA [%] |
| --- | --- | --- | --- | --- | --- | --- |
| Pure ALA | 98.0 | 3.057 | 377.40 | 126 | 100 | 0.0 |
| Comp. Ex. | 15.8 | 4.890 | 27.526 | 36 | 28.3 | 11.3 |
| Ex. 3 | 12.5 | 2.890 | 0 | 0 | 0 | 12.5 |
| Ex. 4 | 13.5 | 4.040 | 0 | 0 | 0 | 13.5 |
| Ex. 5 | 12.7 | 5.662 | 2.673 | 4 | 3.2 | 12.3 |

Even with a lower alpha-lipoic acid content in the complex, the amount of complexed alpha-lipoic acid is significatly higher in product produced according to the present application (12.3% to 13.5% versus 11.3% in the comparison example).

EXAMPLE 8

Temperature Stability at 25° C.

Alpha lipic acid/cyclodextrin complexes were stored in a closed polypropylene container at 25° C. Samples were taken from time to time and the alpha-lipoic acid content was measured via HPLC according to example 6. The initial alpha-lipoic acid content was set to 100%.

Results:

| Days of storage | Content ALA [%] Pure ALA | Content ALA [%] Example 5 |
| --- | --- | --- |
| 0 | 100 | 100 |
| 5 | | 100 |
| 14 | | 100 |
| 39 | 100 | |
| 45 | | 97 |
| 67 | 100 | |
| 76 | | 97 |
| 107 | 100 | |
| 135 | | 97 |

The pure alpha-lipoic acid is stable at room temperature. The alpha-lipoic acid in the cyclodextrin complex according to this invention is also stable at room temperature after some small initial losses, which correspond to the uncomplexed alpha-lipoic acid in the complex (the complex in example 5 has 3% uncomplexed alpha-lipoic acid according to DSC measurements in example 7).

EXAMPLE 9

Temperature Stability at 40° C.

Alpha-lipoic acid/cyclodextrin complexes were stored in a closed polypropylene container in a drying oven at 40° C. Samples were taken from time to time and the alpha-lipoic acid content was measured via HPLC according to example 6. The initial alpha-lipoic acid content was set to 100%.
Results:

| Days of storage | Content ALA [%] Pure ALA | Content ALA [%] Example 5 |
|---|---|---|
| 0 | 100 | 100 |
| 5 |  | 97 |
| 8 | 99 |  |
| 14 |  | 96 |
| 28 |  | 94 |
| 39 | 48*) |  |
| 45 |  | 93 |
| 59 |  | 87 |
| 76 |  | 86 |
| 81 | 41*) |  |
| 107 |  | 86 |
| 135 |  | 86 |

*)difficult to obtain a homogeneous sample, because product polymerizes

The alpha-lipoic acid in the cyclodextrin complex according to this invention shows a significantly higher stability than the pure alpha-lipoic acid and stays stable at 40° C. after some initial losses.

EXAMPLE 10

Temperature Stability at 100° C.

Alpha-lipoic acid/cyclodextrin complexes were stored in closed glass containers in a drying oven at 100° C. Samples were taken from time to time and the alpha-lipoic acid content was measured via HPLC according to example 6. The initial alpha-lipoic acid content was set to 100%.
Results:

| Days of storage | Content ALA [%] Pure ALA | Content ALA [%] Comparison Example | Content ALA [%] Example 3 |
|---|---|---|---|
| 0 | 100 | 100 | 100 |
| 3 | 38 | 85 |  |
| 6 |  |  | 96 |
| 9 |  |  | 93 |
| 11 | 13 |  |  |
| 13 |  |  | 91 |
| 14 |  | 77 |  |
| 24 |  | 72 |  |
| 28 | 4 |  |  |
| 36 | 0 |  |  |
| 53 |  |  | 80 |
| 55 |  | 35 |  |
| 84 |  |  | 77 |
| 112 |  |  | 72 |
| 125 |  | 10 |  |
| 143 |  |  | 66 |
| 173 |  |  | 60 |
| 213 |  |  | 54 |

The half life of pure alpha-lipoic acid under the described storage condition at 100° C. is less than three days. The half life of alpha-lipoic acid complex (example 3) is more than 213 days. This means the complex produced according to this invention under these conditions is more than 70 times more stable than the pure alpha-lipoic acid itself (213d/3d). Even after 213 days of storage at 100° C. still 54% of the original alpha-lipoic acid content is not degraded, whereas only 10% can be detected in product produced according the Canadian patent 2,135,535 just after 125 days.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An alpha-lipoic acid/cyclodextrin composition comprising:
   an alpha-lipoic acid/cyclodextrin complex which has been prepared by acidifying, with an acid, a solution of alpha-lipoic acid prepared by solubilizing alpha-lipoic acid with the aid of a base;
   non-complexed alpha-lipoic acid, if present, being less than 10 dry weight percent, based on Differential Scanning calorimetry, wherein a molar ratio of cyclodextrin to alpha-lipoic acid in the alpha-lipoic acid/cyclodextrin composition is greater than 1.0 and smaller than 2.0;
   wherein the alpha-lipoic acid/cyclodextrin composition contains a salt of the acid and base.

2. The alpha-lipoic acid/cyclodextrin composition of claim 1, wherein the alpha-lipoic acid/cyclodextrin complex has a half life of more than 213 days at 100 degrees Celsius, and the cyclodextrin of the alpha-lipoic acid/cyclodextrin complex is α-cyclodextrin.

3. The alpha-lipoic acid/cyclodextrin composition of claim 1, wherein the non-complexed alpha-lipoic acid, if present, is less than 8 dry weight percent.

4. The alpha-lipoic acid/cyclodextrin composition of claim 1, wherein the non-complexed alpha-lipoic acid, if present, is less than 5 dry weight percent.

5. The alpha-lipoic acid/cyclodextrin composition of claim 1, wherein a molar ratio of cyclodextrin to alpha-lipoic acid in the alpha-lipoic acid/cyclodextrin composition is greater than 1.0 and smaller than 1.5.

6. The alpha-lipoic acid/cyclodextrin composition of claim 1, wherein a molar ratio of cyclodextrin to alpha-lipoic acid in the alpha-lipoic acid/cyclodextrin composition is greater than 1.0 and smaller than 1.2.

7. The alpha-lipoic acid/cyclodextrin composition of claim 1, wherein a molar ratio of cyclodextrin to alpha-lipoic acid in the alpha-lipoic acid/cyclodextrin composition is greater than 1.0 and smaller than 1.15.

8. An alpha-lipoic acid/cyclodextrin composition, comprising:
   a liquid mixture of an alpha-lipoic acid/cyclodextrin complex and a liquid, the liquid mixture having a pH less than pH 7.

9. The alpha-lipoic acid/cyclodextrin composition of claim 8, wherein alpha-lipoic acid of the alpha-lipoic acid/cyclodextrin complex is in an acidic form.

10. The alpha-lipoic acid/cyclodextrin composition of claim 8, wherein the liquid includes water.

11. The alpha-lipoic acid/cyclodextrin composition of claim 8, wherein the liquid includes a mixture of water and an organic solvent.

12. The alpha-lipoic acid/cyclodextrin composition of claim 8, wherein the alpha-lipoic acid/cyclodextrin composition has a solids content of less than 50 percent by weight.

13. The alpha-lipoic acid/cyclodextrin composition of claim 8, wherein the liquid mixture has a pH between pH 6 and pH 3.

14. The alpha-lipoic acid/cyclodextrin composition of claim 8, wherein the non-complexed alpha-lipoic acid, if present, is less than 10 dry weight percent, based on Differential Scanning calorimetry.

15. The alpha-lipoic acid/cyclodextrin composition of claim 8, wherein a molar ratio of cyclodextrin to alpha-lipoic acid of the alpha-lipoic acid/cyclodextrin composition is greater than 1.0 and smaller than 2.0.

16. The alpha-lipoic acid/cyclodextrin composition of claim 8, wherein the liquid includes an organic solvent.

17. The alpha-lipoic acid/cyclodextrin composition of claim 1, wherein the cyclodextrin of the alpha-lipoic acid/cyclodextrin complex is alpha cyclodextrin.

18. The alpha-lipoic acid/cyclodextrin composition of claim 1, wherein the base includes at least one of ammonium hydroxide, sodium hydroxide and potassium hydroxide.

19. The alpha-lipoic acid/cyclodextrin composition of claim 1, wherein the acid includes at least one of hydrochloric acid, sulphuric acid, phosphoric acid, acetic acid, citric acid and ascorbic acid.

20. The alpha-lipoic acid/cyclodextrin composition of claim 1 in the form of a dry powder.

* * * * *